United States Patent [19]
Mick et al.

[11] Patent Number: 5,561,698
[45] Date of Patent: Oct. 1, 1996

[54] RADIOGRAPHIC CALIBRATION DEVICE FOR A MACHINE WITH A MOVABLE RADIATION SOURCE

[75] Inventors: Felix W. Mick, Bronxville; Kenneth R. Zabrouski, Bethpage, both of N.Y.

[73] Assignee: Mick Radio Nuclear Instruments, Inc., Bronx, N.Y.

[21] Appl. No.: 461,534

[22] Filed: Jun. 5, 1995

[51] Int. Cl.⁶ .................................................. H05G 1/28
[52] U.S. Cl. .......................... 378/162; 378/163; 378/207
[58] Field of Search ................................. 378/162, 163, 378/164, 182, 185, 187, 204, 207

[56] References Cited

U.S. PATENT DOCUMENTS

| | | | |
|---|---|---|---|
| 2,293,324 | 8/1942 | Vladeff | 378/162 X |
| 3,991,310 | 11/1976 | Morrison | 378/205 X |
| 4,181,859 | 1/1980 | Vitalini | 378/164 |
| 5,239,569 | 8/1993 | Saleh et al. | 378/163 |

*Primary Examiner*—David P. Porta
*Attorney, Agent, or Firm*—Arthur G. Yeager

[57] ABSTRACT

A film pack holder having a built in scale for use in calibrating the positioning accuracy of an irradiation device to move a radiation source a selected distance along a given path.

20 Claims, 2 Drawing Sheets

RADIOGRAPHIC CALIBRATION DEVICE FOR A MACHINE WITH A MOVABLE RADIATION SOURCE

TECHNICAL FIELD

This invention is in the field of medical devices to provide high doses of radiation; more particularly, a film pack holder that will provide a radiographic image of the positioning accuracy of the radiation source.

BACKGROUND OF THE INVENTION

In the medical treatment of tumors there is a field of brachytherapy which involves a means for radiating the tumor itself or tissue very close thereto. The way in which the radiation is provided generally involves the placement of a very small diameter tube into the tumor. The tube forms a pathway to introduce a tiny portion of a radioactive material, e.g., iridium-192 to various positions in the tube for various dwell times to provide the amount of gamma radiation prescribed by the physician. The positioning of the radiation source is accomplished by a remote control device which permits the operator to be shielded from the radiation given to the patient. It, therefore, is readily understood that the machine must be able to accurately position the radiation source where it is intended to be. In the past a radiographic image was made of the radiation source controlled by an automatic stepping program, e.g., a program which commands movement of the radiation source a first given distance, remains for a given length of time, moves the source a second given distance, and remains for a given time, etc. The distance between radiation images was then measured on the radiograph and compared to the commands. A beginning location was normally set by puncturing the film wrapper by a pin at a known location. This technique for calibration has not been sufficiently accurate or reproducible to satisfy the physician. Accordingly, this invention provides an accurate means to verify the movement of the radiation source, now generally controlled by a computer and its software.

It is an object of this invention to provide a device for accurately measuring the movement of a radiation source by a high dose rate irradiating machine. It is another object of this invention to provide such a device that provides a radiograph of radiation spots superimposed on a scale. Still other objects will become apparent from the more detailed description which follows.

BRIEF SUMMARY OF THE INVENTION

This invention relates to a film holding device for use in calibrating the accuracy of positioning a radioactive source in a machine having a movable radiation source, the holding device comprising an upper and lower flat horizontal plate, spaced apart sufficiently to receive a radiographic film pack therebetween; said lower plate having in the plane of the upper face thereof a slender hollow linear tube adapted to receive slidably therein said radiation source and perpendicular to said tube a plurality of spaced lengths of wire having a density of at least 11.3, said lengths of wire being equally spaced apart a known distance; and means to clamp said two plates together on opposite sides of said film pack.

In specific and preferred embodiments the holder includes locating and aligning studs which cause the film pack to be accurately located in the holder; the holder includes a built-in measurement scale which appears on the radiograph of the radiation source travel; and the holder is made of plastic and includes a built-in tube to simulate the guide tube in the patient's tumor.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
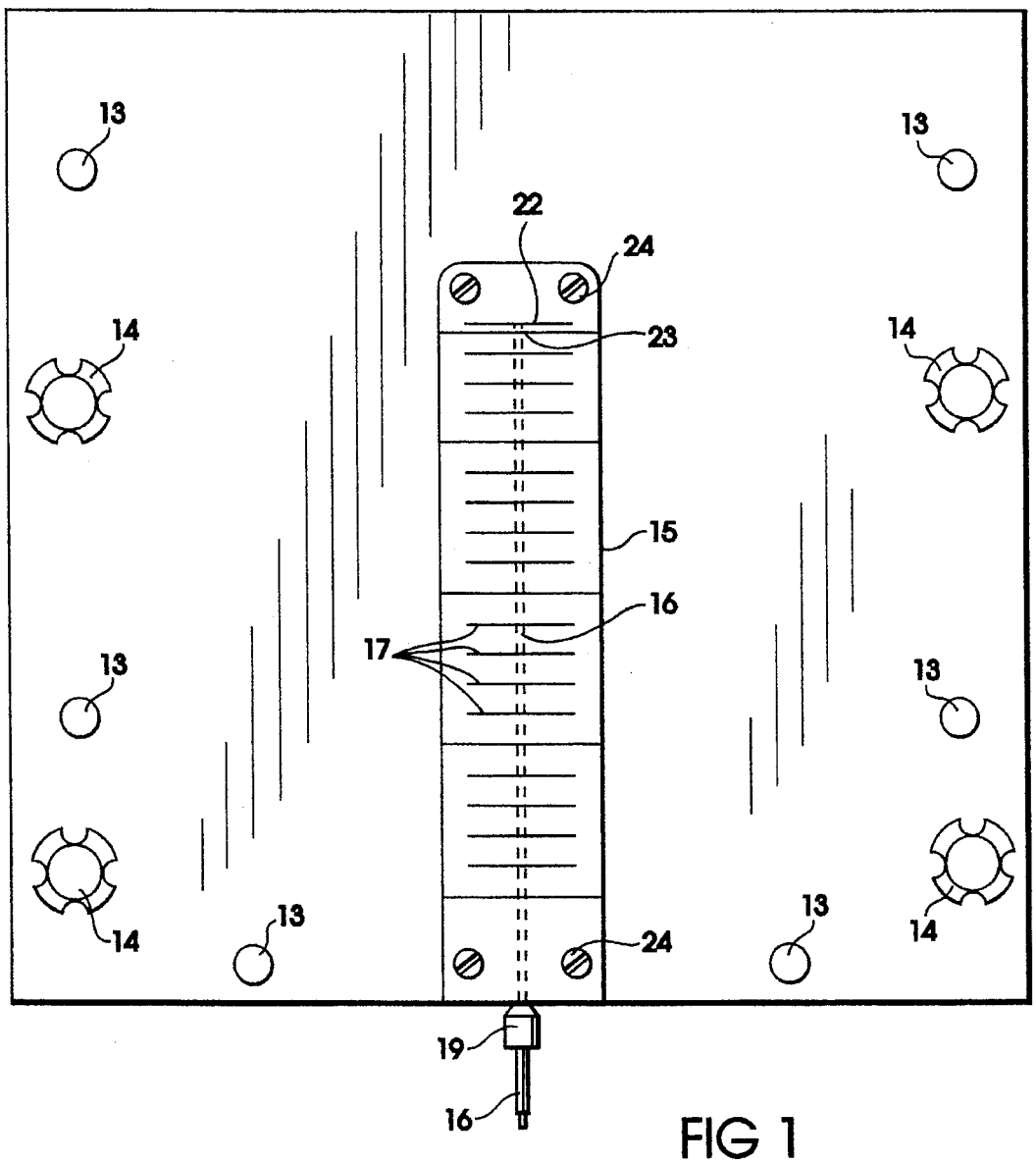
FIG. 1 is a top plan view of the film holder of this invention.
Figure 2:
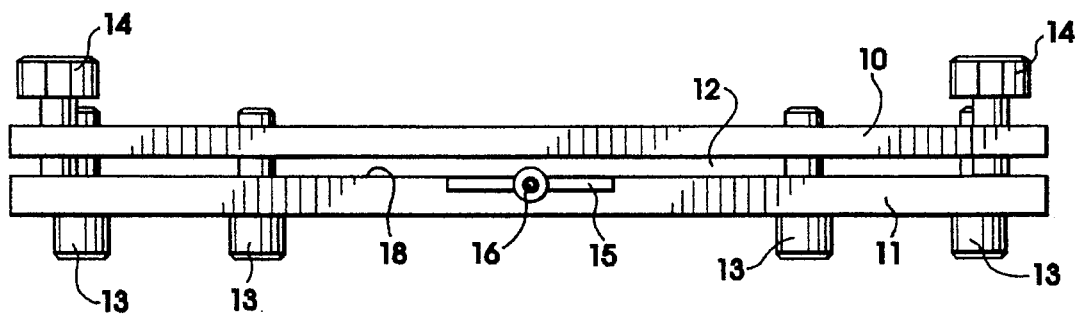
FIG. 2 is a front elevational view of the film holder of this invention.

The invention is best understood by reference to the attached drawings. In FIGS. 1–2 there is shown the details of the film holding device of this invention.

The invention comprises two flat planar plates 10 and 11, generally rectangular in shape so as to hold a rectangular film pack. A suitable film pack includes a 10×12 inch radiographic film wrapped in paper so as to be opaque to ordinary light in a building. The pack of radiographic film is common in the industry and usually is designed to have a rectangular shape with side edges forming its perimeter which fits snugly inside the aligning studs 13. The aligning studs thus position the film pack and holds it steady while locking screws 14 are tightened by hand to clamp the film pack immobile between plates 10 and 11.

Inlaid in the top surface 18 of lower plate 11 is a scale 15 and a slender tubular guide 16. Scale 15 consists of a plurality (typically 20) of short lengths of wire spaced apart a convenient distance, e.g., one centimeter. The last wire 22 at the top of the scale is not part of the scale, but rather represents the upper end of tube 16. In the case of high dose rate remote afterloading devices, which are frequently calibrated by the film holding device of this invention, the radiation source is placed on a long thin arm which slides inside of tube 16. When calibrated, the arm (not shown in the drawings) is inserted fully into tube 16 until it touches the upper end of tube 16. At this position the center of the radiation source is at 23, the top of a scale of twenty centimeters. It is, of course, not critical that the scale be in centimeters; it could be in portions of centimeters, millimeters, inches, or otherwise.

In these drawings the scale is shown to be a thin piece of plastic and the distance markers are short lengths of wire. Tungsten is a preferred metal for wire 17 because it shows sharply in white or light on the radiographic film. Other suitable metals are iridium, gold, lead and tantalum. In general, the suitable metals have a density of at least 11.3.

Scale 15 is shown as a thin plate inlaid into top surface 18 of lower plate 11. Screws 24 hold scale 15 tightly in its inset so that the top surface of scale 15 is flush with top surface 18 of lower plate 11.

Tube 16 extends from outside of plate 11 at its lower edge to line 22 on scale 15. This small tube is about 1–5 mm. in diameter, preferably 1–2 mm. This is large enough to receive and guide the radiation source, a small piece of iridium-192 or other radioactive material, on the distal end of a long thin arm extending outwardly from the remotely controlled radiation machine. The tube, usually stainless steel, although other metals may be operable; is held in place by a fitting 19, sometimes called a "tandem".

Figure 4:
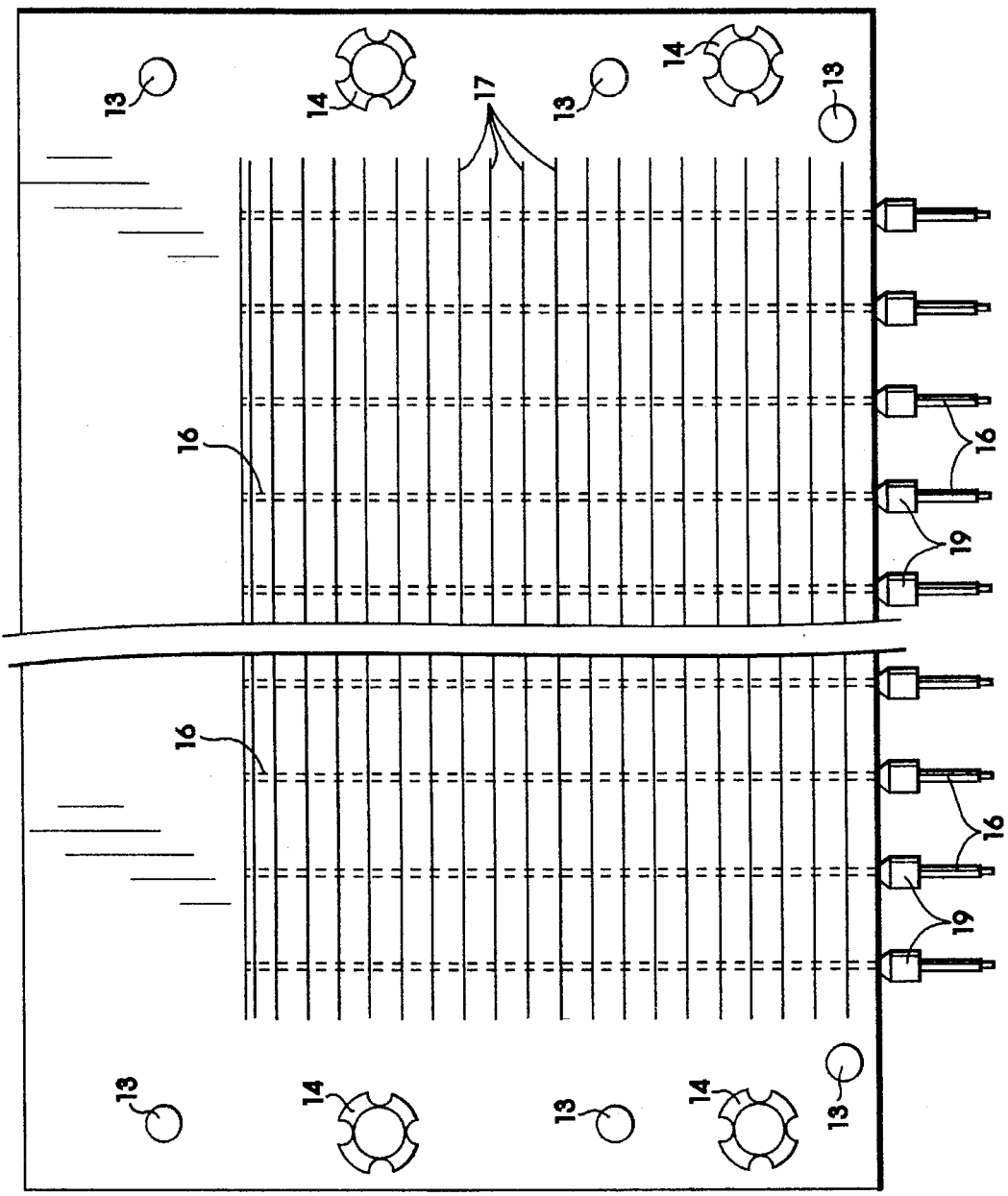
FIG. 4 is a top plan view of a film holder of this invention adapted to receive a plurality of radiation sources for calibration.

In FIG. 4 there is shown a different embodiment of the film holding device of this invention, particularly, one that contains a plurality of tubes 16 and scale wires 17 so as to accommodate a plurality of connections to radiation sources, permitting the calibration of several radiation sources simultaneously or serially. FIG. 4 shows a lower plate 11 but not an upper plate 10, since the upper plate 10 would be identical to that shown in FIGS. 1–2.

Figure 3:
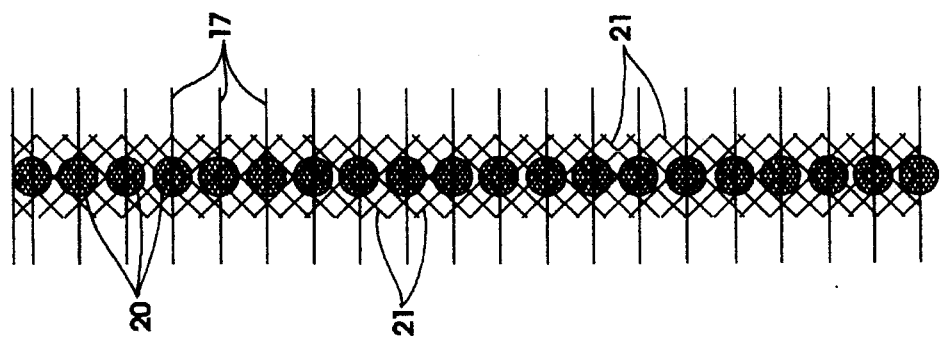
FIG. 3 is a schematic view of a positive representation of a negative radiograph taken widen using the film holder of this invention to calibrate the positioning accuracy of a radiation source moved along a path by a high density radiation machine.

In FIG. 3 there is shown a schematic drawing of a positive of the normal radiographic film exposed to a series of 20 positions (each 1 cm. apart) of a radiation source moving as it might through a tube placed in a human tumor. At each position the radiation source remains in place for a short period of time. In the technical jargon of the radiation operator the radiation source has a series of positions with a "dwell time" of one second at each position. Each position exposes the film to produce a black spot 20 (in reality a light spot on the negative) which is superimposed on an image of the scale (also light on the negative). If the machine is accurate in its movements each black spot 20 will be positioned directly on a wire image 17.

There is a fluorescent scattering of the gamma rays from the radiation source when those rays hit the tungsten wires 17. This produces the scattered light 21 which is less dense (lighter gray) than the heavy black of the spots 20 (in reality light spots on the negative). If the result on the radiographic records does not show precise alignment, the radiation machines movement components are adjusted so the physician can be sure of the proper positioning when treating the patient. The calibration is required at least once each day of operation to maintain proper accuracy.

Plates 10 and 11 may be made of any material which is transparent to the radiation emitted by the radiation source. Preferably, plates 10 and 11 are plastic, such as acrylic plastic material; especially polymethylmethacrylate (commonly known as "Lucite" or "Plexiglass"). It is especially preferred for top plate 10 to be clear transparent plastic, while bottom plate 11 is pigmented with white pigment so as to be translucent.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A film holding device for use in calibrating the accuracy of positioning a radioactive source in a machine having a movable radiation source, the holding device comprising an upper and a lower flat horizontal plate, spaced apart sufficiently to receive a radiographic film pack therebetween; said lower plate having in the plane of the upper face thereof a slender hollow linear tube adapted to receive slidably therein said radiation source and perpendicular to said tube a plurality of spaced lengths of wire having a density of at least 11.3, said lengths of wire being equally spaced apart a known distance; and means to clamp said two plates together on opposite sides of said film pack.

2. The device of claim 1 wherein said known distance is one centimeter.

3. The device of claim 1 wherein said tube is a 3 mm. diameter stainless steel tube.

4. The device of claim 1 wherein said wire is tungsten wire.

5. The device of claim 1 in which said film pack is a paper wrapped, ready pack V-film measuring 10×12 inches.

6. The device of claim 1 wherein said wire is made of a metal selected from the group consisting of tungsten, iridium, gold, lead and tantalum.

7. The device of claim 1 wherein said plates are acrylic polymer materials.

8. The device of claim 7 wherein said plates are polymethylmethacrylate.

9. The device of claim 8 wherein said top plate is transparent, clear polymethylmethacrylate and said bottom plate is translucent white pigmented polymethylmethacrylate.

10. The device of claim 1 wherein said machine is a mobile high dose rate remote-afterloading device for use in brachytherapy.

11. The device of claim 1 wherein said spaced wires extend laterally across substantially all of the upper surface of said lower plate, and said upper surface contains a plurality of said hollow linear tubes spaced laterally apart, each of which is adapted to receive said radiation source slidably therein.

12. A radiographic film holding device for use in calibrating the position accuracy of a high dose rate remote afterloading machine for use in providing radiation to the human body at a plurality of spaced positions; said radiographic film holding device comprising two flat, planar plates of acrylic polymer plastic, spaced apart from each other to receive a radiographic film pack clamped therebetween in sandwich fashion; said lower plate having an upper surface in which is embedded a scale of a plurality of parallel tungsten wires spaced apart at one-centimeter intervals and a small diameter stainless steel tube perpendicular to said wires and adapted to receive slidably therein a radiation source; means to align said radiographic film pack and means to releasably clamp said plates against said film pack.

13. The device of claim 12 wherein said wire is tungsten wire.

14. The device of claim 12 wherein said wire is made of a metal selected from the group consisting of tungsten, iridium, gold, lead and tantalum.

15. The device of claim 12 wherein said spaced wires extend laterally substantially across said lower plate, at least one additional hollow linear tube spaced laterally from said tube, each said tube and at least one additional tube being adapted to receive the radiation source slidably therein in a sequential manner.

16. A film holding device for use in calibrating the accuracy of positioning a radioactive source in a machine having a movable radiation source, the holding device including a pair of flat plates, spaced apart sufficiently to receive a radiographic film pack therebetween; the improvement characterized by a slender hollow linear tube attached to one of said plates and adapted to receive slidably therein the radiation source, a plurality of lengths of wire attached to said one plate and extending perpendicular to said tube and having a density of at least 11.3, said lengths of wire being equally spaced apart a predetermined distance, and releasable means to clamp said plates together with the film pack therebetween.

17. The device of claim 16 wherein said predetermined distance is one centimeter.

18. The device of claim 16 wherein said wire is tungsten wire.

19. The device of claim 16 wherein said wire is made of a metal selected from the group consisting of tungsten, iridium, gold, lead and tantalum.

20. The device of claim 16 wherein said spaced wires extend laterally substantially across said one plate, at least one additional hollow linear tube spaced laterally from said tube, each said tube and at least one additional tube being adapted to receive the radiation source slidably therein in a sequential manner.

* * * * *